United States Patent [19]

Gerhart et al.

[11] 4,446,151

[45] May 1, 1984

[54] DECARBOXYLASE-INHIBITING FLUORINATED PENTANE DIAMINE DERIVATIVES

[75] Inventors: Fritz Gerhart, Kehl-Leutesheim, Fed. Rep. of Germany; Viviane Van Dorsselaer, Strasbourg, France

[73] Assignee: Merrell Toraude et Compagnie, Strasbourg, France

[21] Appl. No.: 407,238

[22] Filed: Aug. 11, 1982

[51] Int. Cl.³ .................. A61K 31/195; C07C 87/26; C07C 101/10; A61K 31/13
[52] U.S. Cl. .................................. 424/319; 562/561; 564/502; 564/509; 424/325
[58] Field of Search ............... 562/561; 564/502, 509; 424/319, 325

[56] References Cited

U.S. PATENT DOCUMENTS 4,049,708  9/1977  Kollonitsch .................. 424/319
4,326,071  4/1982  Bey et al. ..................... 562/561
4,351,954  9/1982  Muramatsa et al. ........... 424/319
4,353,828  10/1982  Bey et al. ..................... 564/509

Primary Examiner—Natalie Trousof
Assistant Examiner—Raymond Covington
Attorney, Agent, or Firm—William J. Stein; Raymond A. McDonald; Stephen L. Nesbitt

[57] ABSTRACT

Novel fluorinated diamine derivatives are inhibitors of ornithine decarboxylase enzyme and have the following general Formula I:

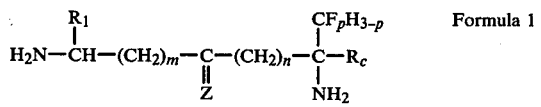

Formula 1 wherein:
$R_c$ represents hydrogen or carboxy;
$R_1$ represents hydrogen or $C_1$–$C_6$ alkyl;
Z represents methylene or oxygen;
m and n each represent 0 or 1 but m+n=1; and
p represents 1 or 2.

18 Claims, No Drawings

DECARBOXYLASE-INHIBITING FLUORINATED PENTANE DIAMINE DERIVATIVES

FIELD OF THE INVENTION

The invention relates to novel pharmaceutically useful fluorinated diamine derivatives which in vivo are inhibitors of a decarboxylase enzyme involved in polyamine formation in living organisms. The invention provides the compounds per se, pharmaceutical compositions comprising said compounds, methods of medical treatment using said compounds, and processes for preparing said compounds.

BACKGROUND OF THE INVENTION

The decarboxylation of ornithine to putrescine, a reaction catalyzed by the enzyme ornithine decarboxylase (ODC), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostate, and thymus; in tumor tissue; in psoriatic skin lesions; and in other cells undergoing rapid growth or proliferation.

Since putrescine is the precursor of both spermidine and spermine, blockade of the conversion of ornithine to putrescine, such as by inhibition of ODC, should prevent new biosynthesis of these polyamines and, thus, provide beneficial physiological effects.

We have disclosed in U.K. Patent Specification No. 2001960A that inter alia compounds of the following Formula A are inhibitors of ornithine decarboxylase:

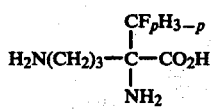

Formula A wherein p represents 1 or 2.

Further, we have disclosed in U.K. Patent Specification No. 2003276A that the analogues of said compounds of Formula A in which hydrogen replaces the carboxy group are likewise ornithine decarboxylase inhibitors.

SUMMARY OF THE INVENTION

The compounds of the invention are represented by the following general formula I:

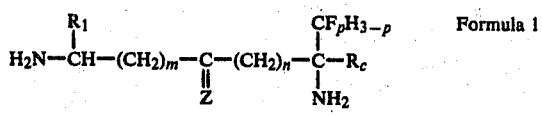

Formula 1 wherein:
$R_c$ represents hydrogen or carboxy;
$R_1$ represents hydrogen or $C_1$-$C_6$ alkyl;
Z represents methylene or oxygen;
m and n each represent 0 or 1 but $m+n=1$; and p represents 1 or 2.

Pharmaceutically acceptable salts and individual optical isomers of the compounds of general Formula I are also within the scope of the invention.

The compounds of Formula I inhibit ornithine decarboxylase enzyme (ODC) in vitro and in vivo, and provide a decrease in putrescine and spermidine concentrations in cells in which active biosynthesis of polyamines is taking place. The compounds of Formula I are useful pharmacological agents for treating those diseases or conditions that are known in the art to be characterized by high ODC activity. In particular, the compounds are useful systemically for treating benign prostatic hypertrophy and for controlling the growth of pathogenic parasitic protozoa in infected domestic animals and humans.

The compounds of Formula I can also be employed to study the presence and physiological function of ODC inhibition in biological systems and its relationship to pathological processes.

It will be recognized that the compounds of Formula I can be substituted at the carboxyl group, if present, and/or at an amino group with any group known in the art to be capable of cleavage in vivo (enzymatically or chemically) to generate a free carboxylic and/or amino group. Compounds which contain such cleavable substituents and which, therefore, can be converted in vivo into a compound of Formula I will be equivalent to the compound of Formula I for the purpose of this invention. Such derivatives can be prepared in manner known per se from the compounds of Formula I. A presently preferred derivative is N-glutamyl.

The ODC activity of the compounds can be determined in vitro by the method described by B. Metcalf et al. *J. Am. Chem. Soc.*, 100, 2551 (1978). The ODC activity of the compounds of Formula I can be determined in vivo by the method of C. Danzin, *Biochemical Pharmacology*, 28, 627 (1979).

DETAILED DESCRIPTION OF THE INVENTION

In general Formula I, $R_c$ represents hydrogen or carboxy.

In general Formula I, $R_1$ represents hydrogen or $C_1$-$C_6$ alkyl, especially methyl, but preferably is hydrogen.

In general Formula I, Z represents a methylene group or an oxygen atom.

In general terms, methylene derivatives (Z is methylene) are presently preferred to keto derivatives (Z is oxygen).

References in this Specification, including the claims, to an alkyl group or moiety mean a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched chain alkyl groups or moieties having 1 to 4 carbon atoms are methyl, ethyl, n-propyl, iso-propyl and n-butyl.

Illustrative examples of straight or branched chain alkyl groups or moieties having 1 to 6 carbon atoms are those specified above having 1 to 4 carbon atoms and n-pentyl, neo-pentyl, n-hexyl and iso-hexyl.

In general Formula I, one of m and n represents 1 and the other of m and n represents 0. Further, p represents 1 or 2. It will be appreciated that when p represents 1, the compounds of the invention are monofluoromethyl derivatives and that when p represents 2 they are difluoromethyl derivatives.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as, organic carboxylic acids, for example salicylic, maleic, malonic, tartaric, citric and ascorbic acids, and organic sulfonic acids, for example methane sulfonic acid; and non-toxic salts formed with inorganic or organic bases, such as, hydroxides of alkali metals, for example, sodium, potassium and lithium, alkaline earth metals, for example, calcium and magnesium, light metals of Group IIIA, for example, aluminium, organic amines, such as, primary, secondary or tertiary amines, for example, cyclohexylamine, ethylamine, methylamino-ethanolamine and piperidine. The salts are prepared by conventional means.

In a preferred embodiment of the invention, there are provided compounds of the following general Formula IA:

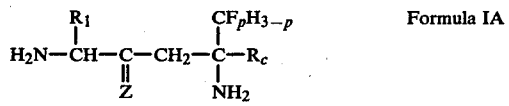

Formula IA wherein $R_1$, $R_c$, $Z$ and $p$ are as defined in connection with Formula I.

In a second embodiment of the invention, there are provided compounds of the following general Formula IB:

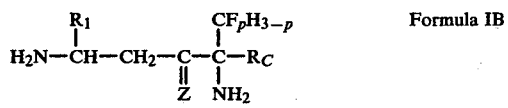

Formula IB wherein $R_1$, $R_c$, $Z$ and $p$ are as defined in connection with Formula I.

Illustrative examples of compounds of the present invention are the following:

1-fluoro-2,5-diamino-4-oxo-pentane;
1,1-difluoro-2,5-diamino-4-oxo-pentane;
1-fluoro-2,5-diamino-4-methylene-pentane;
1,1-difluoro-2,5-diamino-4-methylene-pentane;
2-fluoromethyl-2,5-diamino-4-oxo-pentan-1-oic acid (i.e. 2-fluoromethyl-2,5-diaminolevulinic acid);
2-difluoromethyl-2,5-diamino-4-oxo-pentan-1-oic acid;
2-fluoromethyl-2,5-diamino-4-methylene-pentan-1-oic acid;
2-difluoromethyl-2,5-diamino-4-methylene-pentan-1-oic acid;
1-fluoro-2,5-diamino-3-oxo-pentane;
1,1-difluoro-2,5-diamino-3-oxo-pentane;
1-fluoro-2,5-diamino-3-methylene pentane;
1,1-difluoro-2,5-diamino-3-methylene-pentane;
2-fluoromethyl-2,5-diamino-3-oxo-pentan-1-oic acid;
2-difluoromethyl-2,5-diamino-3-oxo-pentan-1-oic acid;
2-fluoromethyl-2,5-diamino-3-methylene-pentan-1-oic acid;
2-difluoromethyl-2,5-diamino-3-methylene-pentan-1-oic acid;
1-fluoro-2,5-diamino-4-oxo-hexane;
1,1-difluoro-2,5-diamino-3-methylene-heptane;
2-difluoromethyl-2,5-diamino-4-methylene-hexan-1-oic acid;

It is believed that the compounds of general Formula I are "substrate-induced irreversible inhibitors" of ornithine decarboxylase. Such inhibitors are also known in the art as "enzyme-activated irreversible inhibitors", "suicide enzyme inhibitors", "$K_{cat}$ inhibitors", or "mechanism-based inhibitors". In order for a compound to be a substrate-induced irreversible enzyme inhibitor, the compound must be a substrate for the target enzyme, and the compound must contain a latent reactive group susceptible to being unmasked as the results of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the compounds of general Formula I generally exert their action by means of a substrate-induced mechanism, inhibition may occur by other mechanisms, such as by competitive inhibition.

The term "controlling the growth of pathogenic parasitic protozoa", as used herein, means slowing, interrupting, arresting, or stopping the replication of the protozoa in an infected host. The compounds of Formula I are particularly useful against *T.b. brucei* (which causes trypanosomiasis in cattle), *T.b. rhodesiense*, (which causes human sleeping sick-sickness), the coccidia, for example, *Eimeria tenella* (which causes intestinal coccidiosis in fowl (e.g. chickens, turkeys, and ducks)) and the exoerythrocytic form of plasmodia, for example, *plasmodium falciparum* (which causes human malaria).

The antiprotazoal activity of the compounds of Formula I can be demonstrated in vivo or in vitro in standard microbiological test procedures. For example, the activity of the compounds against *T.b. brucei*, and *T.b. rhodesiense* can be determined in infected mice by administering the test compound ad lib daily (3 to 15 days post infection) as a solution in the drinking water. Activity is indicated by an increase in survival time (as compared to untreated controls) or by the absence of parasites in the blood. The activity of the compounds against the coccidia can be determined in infected chickens, for example those infected with *E. tenella* by administering the test compound daily ad lib (from one day pre injection to five days post infection) as a solution in the drinking water. The cecal lesions are evaluated by a standard lesion scoring procedure. (See Reid.

*Am. J. Vet Res.*, 30, 447 (1969) and *Avian Coccidiosis*, P. Long. Editor, British Poultry Science, Ltd., Edinburgh). The activity of the compounds against malaria (*p.faleiparum*) can be determined by a standard in vitro plate culture test (See K. Rieckmann et al, Lancet, 1, 22 (1978)). Antimalarial activity can also be determined in special strains of mice infected with the exoerythrocitic form of *p.berghei*. In this test, the compound is administered ad lib in drinking water starting two days preinfection and continuing 28 days post-infection. Activity is measured by a significant decrease in deaths as compared to controls or by a significant increase in survival time.

The compounds of Formula I wherein $R_c$ is carboxy are also capable of interrupting embryogenesis in female mammals when administered systematically. Thus, the compounds are useful as contragestational agents in female mammals when it is desired to terminate early pregnancy. The contragestational activity of the compounds can be demonstrated in mice by the method of J. Fozard, *European Journal of Pharmacology*, 65, 379 (1980). In general, an effective daily dose of the compounds of Formula I, wherein $R_c$ is carboxy is administered after fertilization during the period between Standard Stages 8–16 of gestation as defined by E. Wischi (See Tables 26–27, pages 82–92, *Biology Data Book*, Altman and Dittmer, Editors, Published by the Federation of American Societies for Experimental Biology, Washington, D.C., 1964). The period of treatment will vary with the species. In humans, the period of treatment will extend from the 6th–7th day of gestation to the 27th day.

The compounds of this invention can be administered in various manners to achieve the desired effect. The compounds can be administered alone or in the form of pharmaceutical preparations either orally or parenterally, for example, subcutaneously, intravenously or interperitoneally. The amount of novel compound administered will vary and can be any effective amount. Depending upon the patient, the condition being treated and the mode of administration, the effective dose of the compound administered may vary from about 5 mg/kg to about 100 mg/kg, of body weight of the patient per day. Unit doses of these compounds can contain, for example, from about 10 mg to 300 mg of the compounds and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described a group of a reactant would be involved in an unwanted reaction under the relevant reaction conditions, the reactive group will be protected in manner known per se by introduction of an appropriate protecting group. The protecting group will be chosen having regard to the nature of the relevant reaction and ease of removal to free the amino group.

In the case where an amino group is to be protected, the protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be, and in some reactions must be, substituted by a single protecting group such as, for example phthaloyl. The protecting groups are introduced in manner known per se by, for example, reaction of the amine with a lower alkanoyl or aroyl chloride, anhydride, sulfonyl chloride, tert-butoxycarbonyloxyimino-2-phenyl-acetonitrile (BOC-ON), or di-tert-butyl dicarbonate (BOC)$_2$O.

Removal of the amino protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; or by hydrogen chloride gas under anhydrous conditions. The use of conditions which will react with the olefinic double bond or of reactants, such as hydrobromic acid, which will react with the olefinic double bond must be avoided. Solvents used will be chosen depending upon the conditions of protecting group removal. For example, ethers such as, for example, diethylether can be used for cleavage using hydrogen chloride gas.

The compounds of Formula I can be prepared in manner known per se by amination of an amino-protected derivative of the corresponding compound of the following general Formula II:

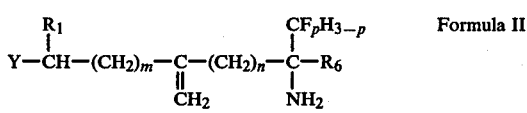

wherein:

$R_1$, m, n and p are as defined in connection with Formula I;

$R_6$ represents hydrogen or cyano; and

Y represents a leaving group such as hydroxy, bromine, chlorine, iodine, tosyloxy (i.e. toluene-p-sulfonyloxy) or mesyloxy (i.e. methanesulfonyloxy), and, when a compound of Formula I in which Z represents oxygen is required, subsequently oxidizing an amino-protected derivative of the corresponding methylene product of said amination.

The reaction preferably proceeds via the corresponding phthalimido derivative as described below.

The amino group in the compound of Formula II is protected in manner known per se during the reaction by a suitable subsequently removable protecting group or groups. When proceeding via the phthalimido derivative when p is 1, it is necessary to use a protecting group which does not leave any hydrogen atom on the amino group in order to obtain the desired compound of Formula I. Usually, the protecting group will be selected so that it is removed during the final step in the conversion of the compound of Formula II into the corresponding compound of Formula I. The presently preferred protecting group is phthaloyl.

The amino-protected derivative of a compound of Formula II with an appropriate leaving group Y can be treated with an alkali metal phthalimide, especially sodium or potassium phthalimide, in a polar organic solvent, such as, for example, dimethylformamide, dimethylsulfoxide or hexamethylphosphoric triamide, to form the corresponding phthalimido derivative. Any of the leaving groups Y exemplified above except hydroxy is appropriate for this reaction. Conveniently one to three equivalents of the phthalimide salt are used per equivalent of compound of Formula II at a temperature of 25° to 100° C. for a period of 0.5 to 48 hours.

When Y is hydroxy, the amino-protected derivative of a compound of Formula II can be converted into the phthalimido derivative by reaction with phthalimide in the presence of a trialkyl- or triaryl-phosphine and diethylazodicarboxylate in an anhydrous aprotic solvent. Usually 1 to 3 equivalents each of phthalimide, the phosphine and diethyldiazodicarboxylate will be used per equivalent of alcohol reactant at a temperature of 10° C. to 100° C. for a period of 18 to 24 hours.

When $R_6$ is hydrogen, the phthalimido derivative of the compound of Formula II can be converted into the required compound of Formula I by heating with a reactant such as hydrazine or methylamine in a polar organic solvent such as, for example, an alkanol, preferably ethanol. Suitably, the conversion is performed at 50° to 100° C., preferably under reflux conditions, for a period of 3 to 24 hours.

The phthalimido derivative of the compound of Formula II also can be converted into the required compound of Formula I by heating with a strong mineral acid such as hydrochloric acid or sulfuric acid. Said heating also hydrolyses any cyano group represented by $R_6$ to a carboxy group.

Preferably a mixture of hydrochloric and acetic acid is used at a temperature of about 95° C. for up to 72 hours. Acids, such as hydrobromic acid, which are reactive towards olefinic double bonds cannot be used.

When a ketone of Formula I (i.e. Z represents oxygen) is required, it can be prepared by oxidation in manner known per se of a derivative of the corresponding methylene phthalimido derivative of Formula II (i.e. Z represents methylene) in which both amino groups are protected. Suitable oxidizing agents include potassium permanganate, osmium tetraoxide and, presently preferred, ozone. When using ozone, it is preferred to pass the ozone through a solution of the methylene phthalimido derivative in a mixture of a non-protic solvent, for example dichloromethane, and methanol at about −78° C. and subsequently to add dimethylsulfide and allow warm up to room temperature to reduce the ozonide/methanol reaction intermediate to the phthalimido protected derivative of the desired ketone. This phthalimido derivative can be converted into the desired ketone by treatment with a strong mineral acid as described above.

When the phthalimido derivative is derived from a compound of Formula II in which $R_6$ represents cyano, acid hydrolysis yields a mixture of compounds in Formula IA in which $R_c$ represents carboxy and Z represents methylene and of the following general Formula B:

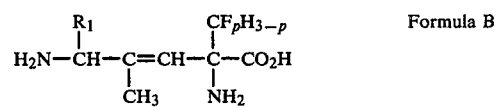

wherein:

$R_1$ and p are as defined in connection with Formula IA. The compounds of Formula IA and Formula B can be separated in manner known per se after derivatisation of the amino and carboxylic functions, for example by first protecting both amino groups by treatment with tert-butoxycarbonyloxyimino-2-phenyl-acetonitrile (BOC-ON) and then forming the methyl ester by treatment with diazomethane, and separation of the di-BOC methyl esters in manner known per se by column chromatography. Subsequently, the separated derivatives can be treated in manner known per se to free the amino groups and/or the carboxy group. In connection with the derivatisation, it has been found that if the ester is formed without first protecting the amino groups, a cylic product is obtained.

Compounds of Formula II in which n is 1 can be obtained in manner known per se from the corresponding compounds of the following general Formula III:

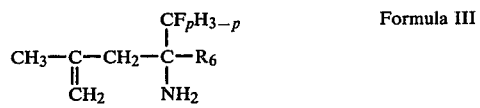

wherein:

$R_6$, and p are as defined in connection with Formula II;

Compounds of Formula II in which n is 1, $R_1$ is hydrogen and Y is halogen can be obtained by halogenation of the corresponding compound of Formula III. Conveniently, the halogenation can be carried out by the Wohl-Ziegler Reaction in which the compound of Formula III is treated with an N-haloamide, preferably an N-bromosuccinimide, usually in the presence of a free-radical initiator such as a peroxide or labile azo compound and under light irradiation.

When $R_6$ is hydrogen, allylic halogenation of the compound of Formula III yields a mixture of the corresponding compound of Formula II and the structural isomer of the following general Formula C:

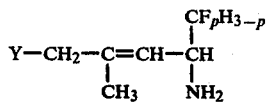 Formula C wherein:
Y represents halogen; and
p is as defined in connection with Formula III.

These compounds can be separated in manner known per se but usually the mixture will be converted via the corresponding phthalimido derivative into a mixture of the corresponding diamines. Said diamines can then be separated by column chromatography of their di-BOC derivatives in the manner described above in connection with separation of acids of Formula IA and Formula B.

Compounds of Formula II in which n is 1, $R_1$ is hydrogen and Y is tosyloxy or mesyloxy can be obtained by allylic oxidation of the corresponding compound of Formula III to form the corresponding alcohol and subsequently treating the alcohol with tosyl chloride or mesyl chloride in the presence of a base such as pyridine.

Compounds of Formula II in which n is 1, $R_1$ is hydrogen and Y is hydroxy also can be obtained from the corresponding compounds of Formula II in which Y is halogen by treatment with sodium acetate and acetic acid and subsequent reduction with, for example lithium aluminium hydride, of the resultant acetate. When a compound of Formula II in which n is 1, $R_1$ is $C_1$–$C_6$ alkyl and Y is hydroxy is required, a compound of Formula II obtained by said reduction is oxidized with, for example, dimethylsulfoxide in the presence of oxalyl chloride and triethylamine at about $-78°$ C. and the resultant aldehyde reacted with, for example, the appropriate alkyl lithium.

Compounds of Formula III in which $R_6$ represents cyano can be obtained from the corresponding compounds of the following general Formula IV by treatment with an alkali metal or ammonium cyanide, such as, for example, sodium cyanide in water in the presence of a water soluble ammonium salt of a strong acid, especially ammonium chloride.

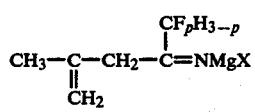 Formula IV wherein:
p is as defined in connection with Formula III; and
X represents bromine, chlorine or iodine Compounds of Formula III in which $R_6$ represents hydrogen, can be obtained from the corresponding compound of Formula IV by reduction with a reducing agent, such as a borohydride, which selectively reduces the imino group.

Compounds of Formula IV can be obtained by treatment of the corresponding Grignard reactant of the following general Formula V with the corresponding fluorinated acetonitrile of the following general Formula VI:

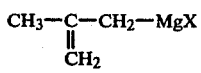 Formula V wherein X is as defined in connection with Formula IV;

 Formula VI wherein p represents 1 or 2.

The Grignard reactants of Formula V can be prepared in manner known per se from, for example, the corresponding halides and magnesium turnings.

Compounds of Formula II above in which n is 1, $R_1$ is hydrogen, $R_6$ is hydrogen or cyano and Y represents bromine or iodine can also be obtained by boron tribromide or trialkylsilyliodide cleavage respectively in manner known per se of a compound of the following general Formula VII:

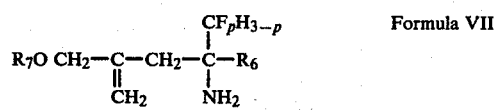 Formula VII wherein:
p is 1 or 2;
$R_6$ represents hydrogen or cyano, and
$R_7$ represents $C_1$–$C_4$ alkyl, preferably methyl.

Compounds of Formula VIII can be obtained from a corresponding compound of the following general Formula VIII by the process steps described above for conversion of a compound of Formula V into a compound of Formula III:

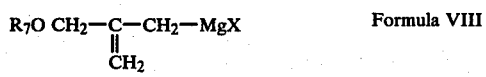 Formula VIII wherein:
$R_7$ is as defined in connection with Formula VII; and
X represents bromine, chlorine or iodine.

Compounds of Formula VIII can be obtained in manner known per se from, for example the corresponding halides and magnesium turnings. The halides also can be obtained in manner known per se. For example the bromide can be obtained by allylic bromination using the Wohl-Ziegler Reaction of the corresponding ether of the following general Formula IX:

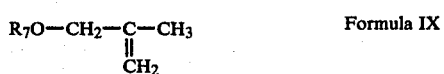 Formula IX wherein $R_7$ is as defined in connection with Formula VIII. The chloride can be obtained by, for example, treating 3-chloro-2-(chloromethyl)-propene with the appropriate sodium alkoxide.

The ethers of Formula IX are known or can be prepared by analogous processes to known ethers. 3-Chloro-2-(chloromethyl)-propene is commercially available as methallyl dichloride.

Compounds of Formula II in which m is 1, $R_1$ is hydrogen, $R_6$ is hydrogen or cyano and Y is hydroxy can be obtained by boron tribromide or trialkylsilyliodide cleavage in manner known per se of an amino-protected derivative of a compound of the following general Formula X.

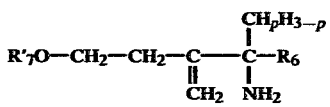

Formula X wherein:
p is 1 or 2;
$R_6$ represents hydrogen or cyano: and
$R_7'$ represents methyl or benzyl;

The reactant of Formula X can be prepared from a corresponding ether analogous to those of the general Formula IX in analogous manner to that described above for the preparation of compound of Formula VII except that, if proceeding via the bromide, bromine is added to the ether and hydrogen bromide subsequently is eliminated by treatment with a strong base instead of allylic bromination.

A more preferred process of preparing the compounds of Formula X commences with the formation of 1-(methoxy or benzyloxy)-3-butene from commercially available 3-butene-1-ol by treatment in manner known per se with potassium tert-butoxide and methyl iodide or benzyl bromide. The ether is converted in manner known per se into a mixture of 1-(methoxy or benzyloxy)-3-bromo-3-butene and its 4-bromo isomer by treatment first with bromine and subsequently with DBU (i.e. diazabicycloundecane). The 3-bromo and 4-bromo isomers can be separated by distillation. The required compound of Formula X is formed from 1-(methoxy or benzyloxy)-3-bromo-3-butene via a Grignard compound in analogous manner to that described above for forming a compound of Formula VII from the corresponding halide.

When a compound of Formula II in which m is 1, $R_1$ is $C_1$-$C_6$ alkyl and Y is hydroxy is required, it can be prepared from the analogous compound of Formula II in which $R_1$ is hydrogen by oxidation and subsequent reaction as described above in the case where n is 1. Compounds of Formula III also can be prepared in manner known per se from the corresponding compounds of the following general Formula XI:

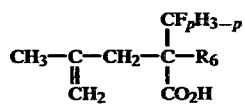

Formula XI wherein:
$R_1$, $R_6$ and p are as defined in connection with Formula III.

The conversion of a compound of Formula XI into a compound of Formula III can be carried out by the Curtius Reaction (see, for example, Organic Reactions, Vol. III at page 338) which proceeds via the corresponding acyl azide and isocyanate.

In an alternative conversion of a compound of Formula XI into a compound of Formula III, the Schmidt Reaction (see, for example, Organic Reactions, Vol. III at page 308) can be used in which the compound of Formula XI is treated with hydrazoic acid in the presence of a strong mineral acid such as, for example sulfuric acid.

A compound of Formula XI also can be converted into a compound of Formula III by the Hofmann Rearrangement (see, for example, Organic Reactions Vol. III at page 268) in which the primary amide of the compound of Formula XI is converted to an amine via the corresponding N-haloamide and isocyanate. According to a preferred procedure for use in the present invention, the amide is treated with iodobenzene bis(trifluoroacetate) in acetonitrile-water (see, for example, Radhakrishna et al J. Org. Chem. 44, (1979), 1746/7). The amide can be obtained from the acid of Formula XI in conventional manner by, for example, forming the acid chloride and treating said chloride with ammonium acetate.

The compounds of Formula XI can be obtained by hydrolysis in manner known per se of the corresponding compounds of the following general Formula XII:

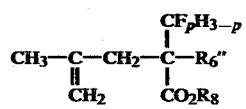

Formula XII wherein:
p is as defined in connection with Formula XII;
$R_6''$ represents cyano or —$CO_2R_9$ where $R_9$ is as defined below;
$R_8$ represents a $C_1$-$C_4$ alkyl group or benzyl; and
$R_9$ represents a $C_1$-$C_8$ alkyl or benzyl.

When a compound of Formula XI is required in which $R_6$ represents hydrogen, a corresponding diester of Formula XII in which $R_8$ and $R_9$ independently represent $C_1$-$C_4$ alkyl, preferably tert. butyl, or benzyl is hydrolysed and decarboxylated by treatment with an acid.

Compounds of Formula XII can be obtained in manner known per se by mono- or di-fluoromethylation of the corresponding compound of the following general Formula XIII:

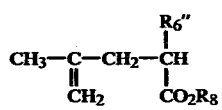

Formula XIII

In Formula XIII, $R_6''$ and $R_8$ are as defined in connection with Formula XII.

The fluoromethylation can be carried out by adding an excess of fluoromethylating agent of the following general Formula XIV to a solution in an aprotic solvent of a carbanion derived from the compound of Formula XIII:

Formula XIV wherein:
p represents 1 or 2; and
W represents bromine, iodine or, preferably, chlorine.

The carbanion usually is obtained by treating the compound of Formula XIII in the aprotic solvent with a base.

The compounds of Formula XIII can be prepared in manner known per se by alkylation of a malonate or cyanoacetate of the following general Formula XV with an alkylhalide of the following general Formula XVI:

Formula XV

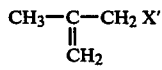

In Formula XV, $R_6''$ and $R_8$ are as defined in connection with Formula XIII and, in Formula XVI, X' represents bromine or chlorine. Suitably the alkylation is carried out in an organic solvent in the presence of a strong base which abstracts a proton from the malonate or cyanoacetate.

It will be appreciated that the order of some of the reaction steps in the process routes described above can be changed. For example, a terminal amino or protected terminal amino group can be introduced into the compound of Formula XII using the same procedure as described for converting the compound of Formula III into a compound of Formula I and subsequently converting, if necessary after protecting the amino group, the resultant compound (which is a compound of the following general Formula XVII or an amino-protected derivative thereof) into a compound of Formula I by the same procedure as described above for converting a compound of Formula XII into a compound of Formula III.

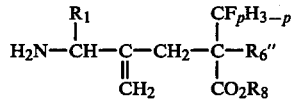

wherein p, $R_1$, $R_6''$ and $R_8$ are as defined in connection with Formula XII. Suitably, the phthalimido intermediate in the said formation of a terminal amino group is subjected to the necessary reaction conditions to convert the $-CO_2R_8$ and, if necessary, $-R_6''$ groups into the required group(s) and subsequently the phthaloyl group is removed.

The compounds of Formula I contain at least one asymmetrical carbon atom and therefore exist as stereoisomers. Methods of separating the stereoisomers of a particular compound will be apparent to those skilled in the art. For example, when $R_1$ is hydrogen, the individual optical isomers of the compounds of Formula I may be separated in manner known per se using optically active acids or bases. In particular, the amino group distal to the fluorinated methyl group can be protected using a ($C_2$-$C_5$ alkoxycarbonyl) phthalimide in a solvent such as, for example tetrahydrofuran, diethyl ether or $C_1$-$C_4$ alkanol, e.g. as methanol or ethanol. The protected amine derivative is then resolved using a chiral acid. The resolved phthalimido compound is then deprotected using, for example, hydrazine or methylamine to remove the phthalimide group followed if required by acid or base hydrolysis to cleave the ester product to obtain the corresponding acid. The thus resolved acids, esters and amines may be employed to prepare the individual isomers of other compounds of the invention in the manner described hereinabove.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable acid addition salts, or are useful for identification or characterisation of the bases.

A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with a inorganic acid may be treated with a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples. All NMR measurements are given on the delta scale (i.e. tetramethylsilane=0).

EXAMPLE 1

Preparation of 1-fluoro-2,5-diamino-4-methylene-pentane, dihydrochloride (A) 1-Fluoro-2-amino-4-methyl-4-pentene

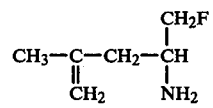

Under an atmosphere of nitrogen, methallylmagnesium chloride is prepared from 97.2 g (4 moles) of magnesium turnings, methallyl chloride (90.6 g, 1 mole) and dry tetrahydrofuran (900 mL). The Grignard solution is separated from the excess of magnesium, cooled to $-40°$ C. and fluoroacetonitrile (56 g, 950 mmoles) in dry tetrahydrofuran (200 mL) is added, dropwise, during about 1 hour. The reaction mixture is kept at $-40°$ C. for an additional 30 minutes, and then poured into a stirred mixture of methanol (2 L), water (50 mL) and sodium borohydride (39 g) cooled at $-40°$ C. After stirring for 1 hour at $-30°$ C., the temperature is allowed to rise to $0°$ C. during 1 hour. After acidification with 6 N hydrochloric acid (about 500 mL) and evaporation, the residue is dissolved in water (about 2 L), and the solution is extracted 3 times with ether to remove non-basic byproducts. The solution is made alkaline with 6 N sodium hydroxide and extracted 3 times with diethyl ether. The organic layer is dried over sodium sulfate and evaporation of the solvent affords 52.5 g of a colored oil (45%).

NMR (CDCl): 1.67 (2H, s, $-NH_2$), 1.77 (3H, s), 2.10 (2H, m), 3.30 (1H, m), 4.33 (2H, d of m, $J_{H-F}=48$ Hz), 4.87 (2H, m).

(B) 1-Fluoro-2-phthalimido-4-methyl-4-pentene

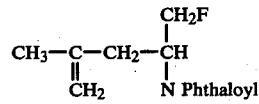

A mixture of 1-fluoro-2-amino-4-methyl-4-pentene (52.5 g, 450 mmoles) prepared as in step A above, N-carbethoxyphthalimide (98.55 g, 450 mmoles), and benzene (600 mL) is kept overnight at room temperature. The solution is concentrated under vacuum, the oily residue is dissolved in methylene chloride (500 mL) and treated with 50 g of triethylamine during 4 hours at room temperature. After extraction with 2 N hydrochloric acid (6×500 mL), the organic layer is dried over sodium sulfate and discoloured by filtration through a layer of silica gel and another of carbon black. The oily residue obtained after concentration (110 g) is extracted several times with petroleum ether to remove some insoluble N-carbethoxyphthalimide. Evaporation of the petroleum ether affords a yellow oil (94 g) which is crystallized from pentane at low temperature (85 g, 77%).

NMR (CDCl₃): 1.77 (3H, s), 2.65 (2H, m), 3.88–5.55 (3H, complex m), 4.70 (2H, broad s), 7.72 (4H, m).

(C)
1-Fluoro-2-phthalimido-4-methylene-5-bromo-pentane

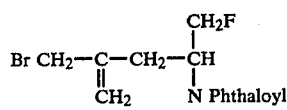

A mixture of 1-fluoro-2-phthalimido-4-methyl-4-pentene (28.3 g, 115 mmoles) prepared as in step B above, N-bromosuccinimide (20.4 g, 115 mmoles), carbontetrachloride (300 mL), and a few mgs of benzoyl peroxide is heated under strong reflux (325 W lamp) during 7.5 hours. After cooling and filtration, the solution is washed with water (100 mL, 3 times), dried over magnesium sulfate and concentrated. The oily residue (quantitative), consisting mainly of the title compound plus some 1-fluoro-2-phthalimido-4-methyl-5-bromo-3-pentene, is used for the next step without further purification.

(D) 1-Fluoro-2,5-diphthalimido-4-methylene-pentane and
1-fluoro-2,5-diphthalimido-4-methyl-3-(E,Z)-pentenes

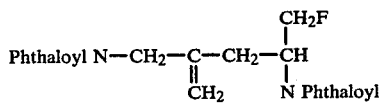

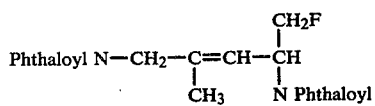

A mixture of 1-fluoro-2-phthalimido-4-methylene-5-bromo pentane (and isomers) (112 g, 345 mmoles) prepared as in step C above and potassium phthalimide (64 g, 345 mmoles) is heated at 80° C. in dry N,N-dimethylformamide (DMF) (200 mL) for 5 hours. After removal of the DMF under vacuum the colored residue is dissolved in chloroform and the organic solution is successively washed with water, twice with 1 N potassium hydroxide, once with 1 N hydrochloric acid and finally twice with brine. The organic solution is dried, discolored by filtration through two layers of silica gel and charcoal, and concentrated. The yellow oil obtained (110 g) is crystallized from ether/petroleum ether to give a mixture of isomers containing mainly 1-fluoro-2,5-diphthalimido-4-methylene-pentane together with some 1-fluoro-2,5-diphthalimido-4-methyl-3-pentene (49 g). The mother liquors (59.7 g) chromatographed on silica gel (1 kg, ethyl acetate/petroleum ether 3/7) give 1-fluoro-2,5-diphthalimido-4-methyl-3-(Z)-pentene (4 g; 2 g after crystallization from ether), a mixture of the three title compounds (6 g) and pure 1-fluoro-2,5-diphthalimido-4-methylene-pentane (13 g). Overall yield of the three isomers: 50%.

NMR data: 1-Fluoro-2,5-diphthalimido-4-methylene-pentane: NMR (CDCl₃): 2.67 (2H, m), 3.93–5.67 (3H, complex m), 4.23 (2H, broad s), 4.93 (2H, broad s), 7.70 (8H, m). 1-Fluoro-2,5-diphthalimido-4-methyl-3-(Z)-pentene: NMR (CDCl₃): 1.70 (3H, broad s), 4.45 (2H, AB, $J_{AB}=8$ Hz), 4.10–5.73 (3H, complex m), 5.85 (1H, m), 7.80 (8H, m). 1-Fluoro-2,5-diphthalimido-4-methyl-3-(E)-pentene (not obtained pure) NMR (CDCl₃): 1.83 (broad s, H₃C¹—C—), 5.80 (m, ¹—C¹=C—H)

(E) 1-Fluoro-2,5-diamino-4-methylene-pentane, dihydrochloride and
1-fluoro-2,5-diamino-4-methyl-3-pentenes

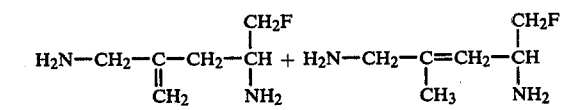

A mixture of 1-fluoro-2,5-diphthalimido-4-methylene pentane and isomers (3.83 g, 10 mmoles) obtained as in step D above and hydrazine hydrate (20 mL of a 1 molar solution in ethanol) is heated for 18 min at 90° C., and after addition of 15 mL of water and 25 mL of conc. hydrochloric acid, heated for an additional 5 min at the same temperature. After complete elimination of the excess of acid by evaporation, the residue is retreated under the same conditions as described above except that the heating with hydrazine hydrate is extended to 30 min. After dissolving the residue in water, removal of phthalhydrazide by filtration, and concentration under vacuum, the residue is dissolved in dry ethanol, and hydrazine dihydrochloride is removed by filtration. Evaporation gives a brownish oil which is used for the next step without further purification.

(F)
1-Fluoro-2,5-di-t-butoxycarbonylamino-4-methylene-pentane and
1-Fluoro-2,5-di-t-butoxycarbonylamino-4-methyl-3-(E)-pentene The oil obtained as in Step E above (10 mmoles), di-t-butyl dicarbonate (5.23 g, 24 mmoles), triethylamine (3.03 g, 30 mmoles), water (6 mL), and tetrahydrofuran (30 mL) are kept at room temperature for 5 hours. After concentration and work-up with chloroform and water, 4.5 g of a colorless oil are obtained which is chromatographed on silica gel (ethyl acetate/petroleum ether: 2/8) to give 1-fluoro-2,5-di-t-butoxycarbonylamino-4-methylene-pentane (1.7 g, 1.34 g after crystallization from ether/petroleum ether at −4° C.) followed by mixed fractions and 1-fluoro-2,5-di-t-butoxycarbonylamino-4-methyl-3-(E)-pentene (1.08 g, 660 mg after crystallization from ether/petroleum ether). Overall yield for the 2 isomers (the cis-pentene derivative is assumed to have been lost during the hydrazine hydrate treatment) is nearly quantitative.

1-Fluoro-2,5-di-tert. butoxycarbonylamino-4-methylene-pentane.

NMR (CDCl$_3$): 1.38(18H, s), 2.25(2H, d, J=7 Hz), 3.67 (2H, d, J=6 Hz), 4.00 (1H, broad m), 4.37 (2H, d of m, J$_{H-F}$=47 Hz), 4.90 (2H, 2—NH—, m), 4.93 (2H, m).

1-Fluoro-2,5-di-tert. butoxycarbonylamino-4-methyl-3-(E)-pentene.

NMR (CDCl$_3$): 1.43 (18H, s), 1.73 (3H, broad s), 3.65 (2H, d, J=7 Hz), 4.35 (2H, d of m, J$_{H-F}$=48 Hz), between 4.0 and 5.0 (3H, 2—NH—, broad m), 5.32 (1H, m).

(G) 1-Fluoro-2,5-diamino-4-methyl-3-(E)-pentene, dihydrochloride

1-Fluoro-2,5-di-t-butoxycarbonylamino-4-methyl-3-(E)-pentene (650 mg, 1.96 mmole) obtained as in step F above is dissolved in dry ether saturated with hydrogen chloride gas. After standing overnight at room temperature, the white solid obtained by decantation is recrystallized from methanol/ether (320 mg, 80%).

NMR (D$_2$O/DCl): 1.85 (3H, broad s), 3.62 (2H, narrow m), 4.53 (1H, broad m), 4.62 (2H, d of m, J$_{H-F}$=46 Hz), 5.52 (1H, m)

Anal. Calcd for C$_6$H$_{13}$N$_2$F.2HCl: C, 35.14; H, 7.37; N, 13.66 Found: C, 35.25; H, 7.13; N, 13.66

(H) 1-Fluoro-2,5-diamino-4-methylene-pentane, dihydrochloride

1-Fluoro-2,5-di-t-butoxycarbonylamino-4-methylene-pentane (650 mg, 1.95 mmole) obtained as in Step F above is dissolved in dry ether saturated with HCl gas. After standing overnight at room temperature, the white solid obtained is recrystallized from methanol/ether (350 mg, 87%).

NMR (D$_2$O/DCl): 2.75 (2H, d, J=8 Hz), 3.68 (2H, broad s), 3.97 (1H, broad m), 4.72 (2H, d of m, J$_{HF}$=48 Hz), 5.42 (2H, broad s)

Anal. Calcd for C$_6$H$_{13}$N$_2$F.2HCl: C, 35.14; H, 7.37; N, 13.66 Found: C, 35.15; H, 7.14; N, 13.69

EXAMPLE 2

Preparation of 1-fluoro-2,5-diamino-4-oxo-pentane, dihydrochloride (A) 1-Fluoro-2,5-di-t-butoxycarbonylamino-4-oxo-pentane

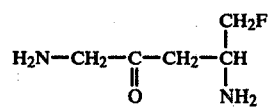

1-Fluoro-2,5-di-t-butoxycarbonylamino-4-methylene-pentane (800 mg, 2.4 mmoles) prepared as in Example 1, Step F, dissolved in a 1/1 mixture (30 mL) of methanol and methylene chloride is cooled to −78° C. and treated with ozone (flow rate 0.3 L/min) for 6 min and 15 sec. An excess of dimethylsulfide is added (about 2 mL) and then the reaction mixture is allowed to warm up to room temperature. After concentration, the residue is extracted twice with methylene chloride/water and work-up of the organic layer affords 800 mg of an oil which is crystallized from ether/petroleum ether (410 mg, 51%).

NMR (CDCl$_3$): 1.42 (18H, s), 2.75 (2H, d, J=6 Hz), 3.40–4.53 (1H, broad m), 3.97 (2H, d, J=6 Hz), 4.38 (2H, d of m, J$_{H-F}$=48 Hz), 5.23 (2H, m, —NH—)

(B) 1-Fluoro-2,5-diamino-4-oxo-pentane, dihydrochloride

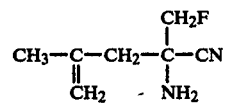

1-Fluoro-2,5-di-t-butoxycarbonylamino-4-oxo-pentane (430 mg, 1.29 mmole) prepared as in Step A above is dissolved in dry ether saturated with hydrogen gas. After standing overnight at room temperature, the slightly colored crystals are treated with charcoal in methanol and recrystallized from methanol/methylene chloride (220 mg, 82%).

NMR (D$_2$O/DCl): 3.20 (2H, d, J=7 Hz), 4.17 (1H, broad m), 4.20 (2H, broad s), 4.73 (2H, d of m, J$_{H-F}$=46 Hz)

Anal. Calcd for C$_5$H$_{11}$N$_2$OF.2HCl: C, 29.00; H, 6.33; N, 13.53 Found: C, 29.11; H, 6.26; N, 13.38

EXAMPLE 3

Preparation of 2-fluoromethyl-2,5-diamino-4-oxo-pentanoic acid, monohydrochloride (A) 2-Fluoromethyl-2-amino-4-methyl-4-pentene-nitrile

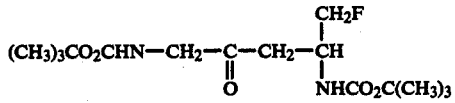

In a 10 L reactor, filled with nitrogen, about 100 mL of a solution of methallyl chloride (453 g, 490 mL, 5.0 moles) in dry tetrahydrofuran (THF) (4 L) is added to a stirred suspension of magnesium turnings (486 g, 20 moles) in THF (1 L), previously activated by 2 mL of methyl iodide. The mixture is heated until Grignard formation starts, then the reactor is cooled with ice and methallyl chloride solution is added at such a rate that the internal temperature does not exceed 50° C. After stirring overnight at room temperature, the Grignard is separated from the excess of magnesium, transferred to a 20 L reactor, and cooled to −40° C. A solution of fluoroacetonitrile (276 g, 253 mL, 4.68 moles) in THF (1 L) is added slowly (within about 15 min), maintaining the internal temperature between −40° and −35° C. Stirring is continued for 30 minutes at −40° C., then the mixture is cooled to −60° C. and hydrolyzed by slow addition of a water/THF mixture (300 mL, 1:1). After that, a solution of ammonium chloride (795 g) and sodium cyanide (490 g) in water (7.5 L), previously cooled with ice, is poured in rapidly, the dry ice bath is removed, and the mixture is stirred for 1 hour at an internal temperature between 0° C. and room temperature. After saturation with sodium chloride (about 2 kg), the organic layer is separated, and the aqueous phase is extracted twice with ether (2×3 L). Drying (Na$_2$SO$_4$) and evaporation gives a dark oil (687 g) which is dissolved in ether (5 L) and extracted carefully with 10% hydrochloric acid (4×650 mL). The combined aqueous phases are cooled with ice and made basic with conc. ammonia. The oil which separates is dissolved in diethyl ether (2.5 L), and the aqueous layer is extracted with diethyl ether (2×2 L). Drying (Na$_2$SO$_4$) and evaporation gives the crude title compound as a dark oil (488 g, 73%) which is used for the next step without further purification.

NMR (CDCl$_3$): 1.93 (3H, s), 2.37 (2H, AB, J$_{AB}$=13 hz), 4.33 (2H, ABX, J$_{AB}$=8 Hz, J$_{AX}$=J$_{BX}$=J$_{H-F}$), 5.0 (2H, m)

(B)
2-Fluoromethyl-2-phthalimido-4-methyl-4-pentene-nitrile

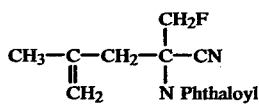

In a 10 L reactor, equipped with a drying tube (CaCl$_2$), a solution of 2-fluoromethyl-2-amino-4-methyl-4-pentene-nitrile obtained as in step A above (488 g, 3.44 moles) and triethylamine (685 g, 6.78 moles) in dry dichloromethane is cooled in an ice bath. A solution of phthaloyldichloride (625 g, 3.1 moles) in dichloromethane (1 L) is added slowly with stirring. After removal of the ice bath, the mixture is stirred at room temperature overnight. After washing with 2 N hydrochloric acid (2×2 L), water (2×2 L), drying (Na$_2$SO$_4$), and evaporation, NMR indicates the presence of some isomer:

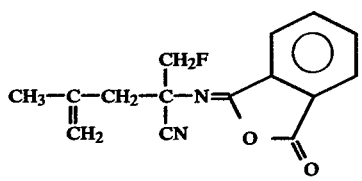

To convert this to the title compound, the crude material is dissolved in dry dichloromethane (4 L), triethylamine (200 mL) is added, and the mixture is refluxed for 4 hours (internal temperature 42° C.). Workup as described in Example 1 Step B gives an oil which solidifies on standing (773 g, 92%).

The solidified oil (60 g portions) is treated in a mortar with ethanol (45 mL), filtered, washed with ethanol (15 mL) and twice with petroleum ether to give 427 g of a yellow solid which is dissolved in benzene (1.3 L), and petroleum ether (2.2 L) is added. After several hours, more petroleum ether is added (1 L), and the mixture is kept at room temperature overnight. Filtration gives pure title material (349 g) (single spot on thin layer chromatography); a second crop is obtained by concentrating the mother liquor. The mother liquor of this second crystallisation is combined with the filtrate of the ethanol washings, evaporated, and chromatographed on silica (2 kg, AcOEt/PE 20:80) to give an additional amount of pure material. Total yield: 471 g (56%).

NMR (CDCl$_3$): 1.88 (3H, s), 2.98 (2H, AB, J$_{AB}$, =13 Hz), 4.85 (2H, m), 5.17 (2H, ABX, J$_{AB}$=9 Hz, J$_{AX}$=J$_{BX}$=J$_{H-F}$=46 Hz), 7.80 (4H, s).

(C)
2-Fluoromethyl-2-phthalimido-4-bromomethyl-4-pentene-nitrile

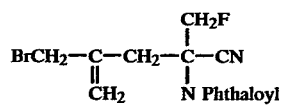

2-Fluoromethyl-2-phthalimido-4-methyl-4-pentene-nitrile obtained as in Step B above (12.38 g, 45.4 mmoles),N-Bromosuccinimide (8.11 g, 45.6 mmoles), dry CCl$_4$ (100 mL), and a few mgs of benzoylperoxide are heated under reflux by irradiation with a lamp (375 W) for 4½ hours. Every hour, some more mgs of benzoylperoxide are added. The reaction is monitored by NMR; after 4½ hours, less than 10% of starting material are left. After cooling to room temperature, succinimide is filtered off. After washing with water (3×100 mL), drying (Na$_2$SO$_4$) and evaporation, the crude title compound is obtained as a solid (14.94 g, 94%) which is used for the next step without further purification.

NMR (CDCl$_3$): 3.20 (2H, AB, J$_{AB}$=13 Hz), 4.10 (2H, AB, J$_{AB}$=11 Hz), 5.10 (1H, s), 5.13 (2H, ABX, J$_{AB}$=9 Hz, J$_{AX}$=J$_{BX}$=J$_{H-F}$=46 Hz), 5.37 (1H, s), 7.73 (4H, s).

(D)
2-Fluoromethyl-2-phthalimido-4-phthalimidomethyl-4-pentene-nitrile

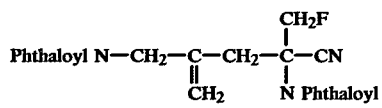

2-Fluoromethyl-2-phthalimido-4-bromomethyl-4-pentene-nitrile obtained as in Step C above (14.94 g, 42.6 mmoles), potassium phthalimide (7.90 g, 42.7 mmoles) and dry dimethylformamide (DMF) (100 mL, refluxed over and distilled from calcium hydride) are heated (bath temperature 70°-80° C.) for 3 hours. The DMF is removed under vacuum (oil pump), the residue is dissolved in chloroform, salts are removed by filtration, and the solution is washed with 1 N sodium hydroxide and several times with water. After drying (Na$_2$SO$_4$), evaporation gives crude title compound as a viscous oil. This is dissolved in chloroform (minimum amount), the same volume of diethyl ether is added, and the same volume of petroleum ether. After standing overnight, the crystals (5.0 g) are collected, and the filtrate is evaporated, and chromatographed on silica (35 g/kg; EcOEt/PE 40:60). Total yield of pure title compound: 8.83 g (50%).

NMR (CDCl$_3$): 3.17 (2H, AB, J$_{AB}$=14 Hz), 4.33 (2H, s), 5.17 (2H, s with fine splitting), 5.23 (2H, ABX, J$_{AB}$=9 Hz, J$_{AX}$=J$_{BX}$=J$_{H-F}$=46 Hz), 7.82 (8H, s with fine splitting).

(E)
2-Fluoromethyl-2,5-diphthalimido-4-oxopentane-nitrile

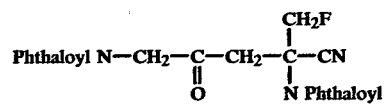

2-Fluoromethyl-2-phthalimido-4-phthalimido-methyl-4-pentene nitrile obtained as in Step D above (2.65 g, 6.32 mmoles), dissolved in a 1:1 mixture (50 mL) of methylene chloride (Baker blue label) and methanol are cooled to −78° C. and treated with ozone (flow rate about 0.3 L/min) for 12¾ minutes (i.e., 2 min/mole). An excess of dimethylsulfide (2 mL) is added, and the mixture is allowed to warm up to room temperature. After standing for 2 hours, the insoluble title ketone (1.73 g, 65%) is collected and washed with a small amount of chloroform and ether. The ketone is used for the next step without further purification.

An analytical sample was obtained by recrystallization from hot tetrahydrofuran (100 mL/3.5 g)/CHCl₃ (100 mL).

Anal. Calcd. for $C_{22}H_{14}FN_3O_5$: C, 63.01; H, 3.37; N, 10.02 found: C, 62.91; H, 3.61; N, 10.03

(F) 2-Fluoromethyl-2,5-diamino-4-oxo-pentanoic acid, monohydrochloride

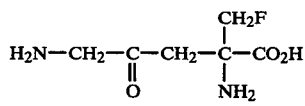

2-Fluoromethyl-2,5-diphthalimido-4-oxo-pentanenitrile obtained as in Step E above (5.78 g, 13.8 mmoles) is heated with conc. hydrochloric acid (50 mL) at 100° C. (bath temperature) for 32 hours. After cooling to room temperature, phthalic acid is removed by filtration, and the filtrate is evaporated. The residue is dissolved in 1 N hydrochloric acid (50 mL) and extracted with ether (3×50 mL). After evaporation, the residue is dried carefully overnight (oil pump). It is dissolved in a 1:1 mixture of methanol and ethanol (80 mL), ammonium chloride is removed by filtration and washed with the same mixture (10 mL). After addition of propylene oxide (3 mL), the mixture is kept at room temperature for several hours, then in the refrigerator overnight. The crude monohydrochloride is collected, washed with a small amount of ethanol and ether and dried (2.14 g). Treatment with 20 weight-% charcoal in water at room temperature for 3½ hours and evaporation gives 2.11 g of colourless material which is recrystallized from water (15 mL) and ethanol. Drying at room temperature under vacuum (oil pump) in the presence of $P_2O_5$ gives the semihydrate 1.60 g (52%), mp 154° C.

NMR (D₂O/DCl): 3.53 (2H, narrow AB, $J_{AB}$=18 Hz), 4.23 (2H, s), 4.87 (2H, d, $J_{H-F}$=46 Hz).

Anal. Calcd. for $C_6H_{11}FN_2O_3$, HCl, ½ H₂O: C, 32.22; H, 5.86; N, 12.53 found: C, 32.25; H, 5.83; N, 12.48

EXAMPLE 4

Preparation of 1,1 difluoro-2,5-diamino-4-methylene-pentane, dihydrochloride (A) 1,1-Difluoro-2-amino-4-methyl-4-pentene

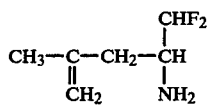

Under an atmosphere of nitrogen, methallyl magnesium chloride is prepared from 21.4 g (880 mmoles) of magnesium turnings, methallyl chloride (19.93 g, 220 mmoles) and dry tetrahydrofuran (THF) (210 mL). The Grignard solution (titration 70%) is separated from the excess of magnesium, cooled to −75° C. and a 1.3 M solution of difluoroacetonitrile in dry (THF) (120 mL, 156 mmoles) is added dropwise in order to keep the temperature hot higher than −70° C. during 1 hour. The reaction mixture is kept at −75° C. for an additional 30 minutes, and a mixture of methanol (300 mL), water (16 mL) and sodium borohydride (5.9 g, 156 mmoles) cooled at −78° C. is poured into the reaction mixture. The temperature is allowed to rise to −10° C. during 1.5 hours and after acidification with 6 N hydrochloric acid and evaporation, the residue is diluted with water, non-basic by-products are extracted with ether, and after basification with 4 N sodium hydroxide, the amine is extracted twice with ether (250 mL). After drying over sodium sulfate, the ether is removed under normal pressure to give an oily residue (21 g, still containing some ether). Bulb to bulb distillation of 200 mg sample gave 110 mg of title amine; b.p. 160° C.

NMR (CDCl₃): 1.05, 2.65 (2H, complex m+2H (NH₂)), 1.77 (3H, s), 3.08 (1H, m), 4.82 (2H, m), 5.57 (1H, d of t, $J_{H-F}$=56 Hz, $J_{H-H}$=4 Hz).

(B) 1,1-Difluoro-2-phthalimido-4-methyl-4-pentene

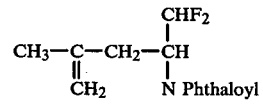

A mixture of crude 1.1-difluoro-2-amino-4-methyl-4-pentene (20 g, evaluated 110 mmoles) prepared as in Step A above, N-carbethoxyphthalimide (24 g, 110 mmoles) in benzene (300 mL) is kept overnight at room temperature. The solution is concentrated under vacuum, the oily residue is dissolved in methylene chloride (400 mL) and treated with 8 g of triethylamine during one night at room temperature. The solution is extracted with water, twice with 1 N hydrochloric acid and twice with water again. Evaporation of the organic layer affords an oily residue which is crystallized from petroleum ether at −5° C. (19.2 g, yield based on methallyl chloride: 45%).

NMR (CDl₃): 1.77 (3H, broad s), 2.22–3.25 (2H, m), 4.63 (1H, m), 4.70 (2H, m), 6.32 (2H, d of t, $J_{H-F}$=57 Hz, $J_{H-H}$=7 Hz) 7.83 (4H, m).

(C) 1,1-Difluoro-2-phthalimido-4-methylene-5-bromopentane

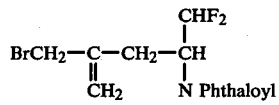

A mixture of 1,1-difluoro-2-phthalimido-4-methyl-4-pentene (17.8 g, 67.2 mmoles) prepared as in Step B above, N-bromosuccinimide (14.4 g, 80.6 mmoles), carbon tetrachloride (200 mL) and benzoyl peroxide (4 times one end of spatula during the heating period) is heated under strong reflux (325 W lamp) during 6.5 hours. After cooling, the solution is extracted 3 times with water, dried over magnesium sulfate, and concentrated. The oily residue obtained is used for the next step without further purification.

NMR (CDCl₃): 2.42–3.25 (2H, m), 3.95 (2H, m), 4.63 (1H, m), 4.98 and 5.18 (2H,2 broad s), 6.32 (d of t, $J_{HF}=56$ Hz, $J_{H-H}=7$ Hz), 7.78 (4H, m).

(D)
1,1-Difluoro-2,5-diphthalimido-4-methylene-pentane

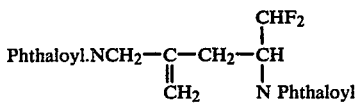

A mixture of 1,1-difluoro-2-phthalimido-4-methylene-5-bromo-pentane (impure, evaluated 67 mmoles) prepared as in Step C above, and potassium phthalimide (13.9 g, 75 mmoles) is heated at 75° C. in dry N,N-dimethylformamide (DMF) (100 mL) for 3 hours. After removal of the DMF under vacuum, the residue is dissolved in chloroform and extracted with 1 N potassium hydroxide and three times with water. Work-up as described in Example 1(D) affords a colored oil (30 g, containing solvents) which is chromatographed on silica gel (petroleum ether/ether acetate: 70/30). The oil obtained (11.3 g) is crystallized from chloroform/ether/petroleum ether to give 1,1-difluoro-2,5-diphthalimido-4-methylene-pentane slightly contaminated (about 15%) by 1,1-difluoro-2,5-diphthalimido-4-methyl-3-pentene (7.9 g of mixture, yield based on 1,1-difluoro-2-phthalimido-4-methyl-4-pentene: 29%).

NMR (CDCl₃): 2.82 (2H, m), 4.25 (2H, broad s), 4.62 (1H, broad m), 4.98 (2H, broad s), 6.27 (1H, d of t, $J_{H-F}=56$ Hz $J_{H-H}=7$ Hz), 7.78 (8H, m).

(E) 1,1-Difluoro-2,5-diamino-4-methylene-pentane, dihydrochloride, crude product

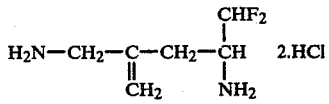

A mixture of 1,1-difluoro-2,5-diphthalimido-4-methylene-pentane (7.77 g, 19 mmoles) prepared as in Step D above, and hydrazine hydrate (38 mL of a 1 M solution in ethanol) is heated for 5 hours at 90° C. After addition of water (30 mL) and concentrated hydrochloric acid (60 mL) heating is continued for one more hour at 90° C. After filtration, and evaporation to dryness, the residue is dissolved in water, and the remaining phthalhydrazide is elimated by filtration. Concentration under vacuum affords an oil which is used without further purification.

(F)
1,1-Difluoro-2,5-di-t-butoxycarbonylamino-4-methylene-pentane

The oil prepared as in Step E above, (19 mmoles), di-t-butyl dicarbonate (9.15 g, 42 mmoles), triethylamine (4.55 g, 45 mmoles) 12 ml of water and 60 ml of THF are kept under magnetic stirring at room temperature for 4 days. After concentration and extraction with water and methylene chloride, work-up as described in Example 1(F) affords a colored oil (8.3 g), which is chromatographed on silica gel (petroleum ether/ethyl acetate: 80/20). 1,1-Difluoro-2,5-di-t-butoxycarbonylamino-4-methylene-pentane is obtained after crystallization (ether/petroleum ether) of the pure fractions (3.3 g, 49%).

NMR (CDCl₃): 1.45 (18H, s), 2.08 (2H, m), 3.73 (2H, broad d, J=6 Hz), 4.08 (1H, broad m), 4.78 (2H, 2-NH-, m), 5.02 (2H, m), 5.83 (1H, t of broad s, $J_{H-F}=56$ Hz).

(G) 1,1-Difluoro-2,5-diamino-4-methylene-pentane, dihydrochloride 1,1-Difluoro-2,5-di-t-butoxycarbonylamino-4-methylene-pentane (3.3 g, 9.4 mmoles) is dissolved in dry ether saturated with hydrogen chloride gas. After standing overnight, the hygroscopic solid obtained is recrystallized twice from methanol/methylene chloride (1.49 g, 71%).

NMR (D₂O/DCl): 2.68 (2H, d, J=8 Hz), 3.72 (2H, broad s), 3.98 (1H, broad m) 5.43 (2H, broad s), 6.32 (t of broad s, $J_{H-F}=54$ Hz).

Anal. Calcd for C₆H₁₂N₂F₂.2HCl: C, 32.30; H, 6.33; N, 12.56; Found: C, 32.17; H, 6.18; N, 12.37.

EXAMPLE 5

PREPARATION OF 2-FLUOROMETHYL-2,5-DIAMINO-4-METHYLENE-PENTANOIC ACID, MONOHYDROCHLORIDE

(A)
2-Fluoromethyl-2,5-diamino-4-methylene-pentanoic acid (crude)

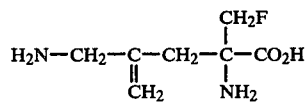

2-Fluoromethyl-2,5-diphthalimido-4-methylenevaleronitrile (3.5 g) prepared as in Example 3, Step D is refluxed with conc HCl for 16 hours. NMR on an aliquot indicates N-phthaloyl cleavage to be incomplete. Heating is continued with fresh conc HCl for 7 more hours. After filtration, the solution is evaporated, the residue is dissolved in water, filtered again, extracted twice with ether, and evaporated to dryness.

The residue is stripped twice with isopropanol, dissolved in isopropanol/ethanol, ammonium chloride is filtered off, and crude aminoacid hydrochloride is precipitated with propylene oxide (about 2 g), yield 0,75 g. Evaporation of the mother liquor gives more material which on recrystallisation (water/ethanol/isopropanol) affords 1.5 g of crude 2-fluoromethyl-2,5-diamino-4-methylene-pentanoic acid, monohydrochloride.

NMR (D₂O/DCl): 3.03 (2H, s), 3.77 (2H, s), 5.07 (2H, AB-part of ABX, $J_{AB}=10$ Hz, $J_{AX}=J_{BX}=J_{H-F}=47$ Hz).

(B). 2-Fluoromethyl-2,5-di (tert-butoxycarbonylamino)-4-methylene-pentanoic acid

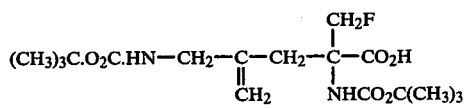

A solution of crude 2-fluoromethyl-2,5-diamino-4-methylene-pentanoic acid, monohydrochloride (1.5 g) obtained in Step A above in water/THF (15 ml/22 ml) is treated with triethylamine (4 g) and di-tert-butyldicarbonate (4 g) at room temperature overnight. THF is distilled off, and the residue is dissolved in water. After acidification (1N HCl, pH about 2), the mixture is extracted with dichloromethane. Re-extraction with 10% aqueous sodium bicarbonate, acidification (1N HCl, pH about 2) and extraction with dichloromethane gives 0.7 g of title compound.

NMR (CDCl₃): 1.43 (18H, s), 2.70 (2H, AB, $J_{AB}=14$ Hz) 3.63 (2H, broad s), 4.83 (2H, AB-part of ABX, $J_{AB}=9$ Hz, $J_{AX}=J_{BX}=J_{H-F}=47$ Hz), 5.07 (2H, broad d), 5.8 (N-H), 9.6 (1H, -O-H).

(C) Methyl 2-fluoromethyl-2,5-di(tert-butoxycarbonylamino)-4-methylene-pentanoate

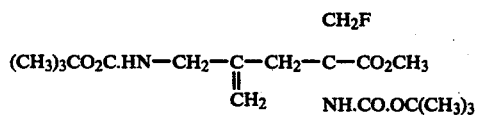

2-Fluoromethyl-2,5-di(tert-butoxycarbonylamino) 4-methylene-pentanoic acid (0.7 g) obtained in Step B above is dissolved in ether, and etheral diazomethane is added until a yellow colour persists Evaporation gives an oil (0.76 g) which is chromatographed on silica (AcOEt/petroleum ether 1:4). Yield of pure product 0.72 g.

NMR (CDCl₃): 1.43 (18.H, s), 2.67 (2H, AB, $J_{AB}=14$ Hz), 3.60 (2H, narrow AB), 3.80 (3H, s), 4.80 (2H, AB-part of ABX, $J_{AB}=9$ Hz, $J_{AX}=J_{BX}=J_{H-F}=47$ Hz), 5.0 (2H, AB), 5.70 (N-H).

(D) Methyl 2-fluoromethyl-2,5-diamino-4-methylene-pentanoate, dihydrochloride

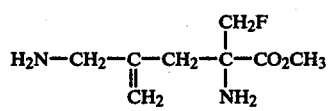

Methyl 2-fluoromethyl-2,5-di(tert-butoxycarbonylamino)-4-methylene pentanoate (0.72 g) obtained in Step C above is treated with dry ether saturated with HCl gas. After stirring overnight the title compound is collected (0.38 g, 78%). Recrystallisation from isopropanol/ethyl acetate gives the pure product yield 300 mg.

Analysis for C₈H₁₇N₂O₂Cl₂F: Calculated C, 34.52; H, 6.51; N, 10.85: Found: C, 36.77; H, 6.07; N, 10.36.

NMR (D₂O): 2.83 (2H, AB, $J_{AB}=14$ Hz), 3.57 (2H, s), 3.93 (3H, s), 4.87 (2H, AB-part of ABX, $J_{AB}=10$ Hz, $J_{AX}=J_{BX}=J_{H-F}=47$ Hz), 5.47 (2H, narrow m).

(E) Pure 2-Fluoromethyl-2,5-diamino-4-methylene-pentanoic acid monohydrochloride

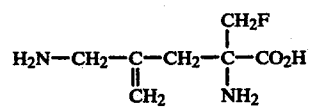

Methyl 2-fluoromethyl-2,5-diamino-4-methylene-pentanoate (150 mg, 0.57 mmoles) is dissolved in a mixture of 2 N NaOH (2 mL) and THF (1.5 mL) and stirred at room temperature for 1 hour. After acidification (1N HCl), the THF is removed under vacuum and the solution is made basic (1N NaOH). After careful extraction twice with diethylether and twice with methylene chloride, the mixture is re-acidified (1N HCl) and evaporated to dryness. After careful drying (oil pump), the residue is digested with dry ethanol and sodium chloride is filtered off. Upon addition of propyleneoxide, the monohydrochloride precipitates. Recrystallisation from water/isopropanol gives 70 mg of colourless material.

In the following Examples relating to pharmaceutical compositions, the term "active compound" is used to indicate the compound 1-fluoro-2,5-diamino-4-methylene-pentane. This compound may be replaced in these compositions by any other compound of the invention, for example by 1-fluoro-2,5-diamino-4-oxo-pentane. Adjustments in the amount of medicament may be necessary or desirable depending upon the degree of activity of the medicament as is well known in the art.

EXAMPLE 6

All illustrative composition of hard gelatin capsules is as follows:

| | |
|---|---|
| (a) active compound | 20 mg |
| (b) talc | 5 mg |
| (c) lactose | 90 mg |

The formulation is prepared by passing the dry powders of (a) and (b) through a fine mesh screen and mixing them well. The powder is then filled into hard gelatine capsules at a net fill of 115 mg per capsule.

EXAMPLE 7

An illustrative composition for tablets is as follows:

| | |
|---|---|
| (a) active compound | 20 mg |
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 8

An illustrative composition for an injectable suspension is the following 1 ml ampul for an intramuscular injection:

| | weight percent |
|---|---|
| (a) active compound | 1.0 |
| (b) polyvinylpyrrolidone | 0.5 |
| (c) lecithin | 0.25 |
| (d) water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

EXAMPLE 9

| | mg/suppository |
|---|---|
| Active Compound | 50 |
| Oil of Theobroma | 950 |

The medicament is powdered and passed through a B.S. No. 100 Sieve and triturated with molten oil of Theobroma at 45° C. to form a smooth suspension. The mixture is well stirred and poured into moulds each of nominal 1 G capacity, to produce suppositories.

EXAMPLE 10

The activity of the compounds of Formula I as inhibitors of ornithine decarboxylase (ODC) can be demonstrated in vitro according to the following procedure:

Orinithine decarboxylase (ODC) is prepared from the livers of rats which have been injected with thioacetamide (150 mg/kg of body weight) 18 hrs before sacrifice, and is purified about ten fold by acid treatment at pH 4.6 as described by Ono et al (Biochem. Biophys. Acta 284, 285 (1972). The stock solution of ODC is composed of proteins (16 mg/mL), sodium phosphate buffer (30 mM, pH 7.1), dithiothreitol (5 mM) and pyridoxal phosphate (0.1 mM). The specific activity of this stock solution is 0.12 nmol of $CO_2$/min per mg of protein. For a typical experiment 320 $\mu$l of this stock solution is mixed at time 0 with 80 $\mu$l of a solution of the inhibitor in water and incubated at 37°. At different times 50 $\mu$l aliquots are transferred into a 1 mL assay medium containing sodium phosphate (30 mM, pH 7.1), dithiothreitol (5 mM), pyridoxal phosphate (0.1 mM), L-ornithine (0.081 $\mu$mol), and DL-[1-$^{14}$C]ornithine (0.043 $\mu$mol, 58 Ci/mol, Amersham) in a closed vessel in which a filter paper moistered with 50 $\mu$l hyamine hydroxide (1M) is fitted. The reaction is allowed to proceed for 60 min at 37° C. and then terminated by addition of 0.5 ml of 40% trichloroacetic acid. After an additional 30 min, the $CO_2$ absorbed on the filter paper is counted in a standard scintillation cocktail. $K_I$ (apparent dissociation constant) and $\tau_{50}$ (half-life, at infinite concentration of inhibitor) are calculated according to the method of Kitz and Wilson (J. Biol. Chem., 237, 3245 (1962)).

When tested according to the above-described procedure, representative compounds of Formula I gave the results shown in Table I below. Half-life ($t_{1/2}$) at 10 $\mu$M is also set forth in Table I.

TABLE I

| Compound | ODC $K_I$ ($\mu$M) | $\tau_{50}$ (Min.) | $t_{\frac{1}{2}}$ (Min.) |
|---|---|---|---|
| A | 4.8 | 3.1 | 4.5 |
| B | 13 | 2.6 | 6.4 |
| C | 7.5 | 1.6 | 2.8 |
| D | 53 | 3.6 | 23 |
| E | 60 | 2.2 | 14 |

In Table I, the following abbreviations have been used:
A—2-fluoromethyl-2,5-diamino-4-oxo-pentanoic acid, (see Example 3).
B—1-fluoro-2,5-diamino-4-methylene-pentane, (see Example 1);
C—1-fluoro-2,5-diamino-4-oxo-pentane, (see Example 2);
D—2-fluoromethyl-2,5-diamino-4-methylene-pentanoic acid, (see Example 5);
E—1,1-difluoro-2,5-diamino-4-methylene-pentane (see Example 4).

We claim:
1. A compound of the following general Formula I:

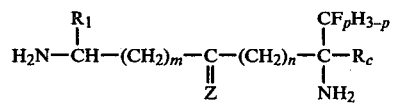

Formula 1 wherein:
$R_c$ represents hydrogen or carboxy;
$R_1$ represents hydrogen or $C_1$-$C_6$ alkyl;
Z represents methylene or oxygen;
m and n each represent 0 or 1 but m+n=1;
p represents 1 or 2,
or a pharmaceutically acceptable salt thereof.

2. A compound as defined in claim 1 and having the following general Formula IA:

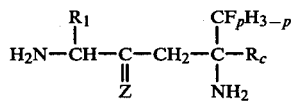

Formula IA wherein $R_1$, $R_c$, Z and p are as defined in claim 1, or a pharmaceutically acceptable salt thereof.

3. A compound as defined in claim 1 and having the following general Formula IB:

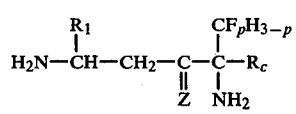

Formula IB wherein $R_1$, $R_c$, Z and p are as defined in claim 1 or a pharmaceutically acceptable salt thereof.

4. A compound as defined in claim 1 wherein Z represents oxygen.

5. A compound as defined in claim 1 wherein Z represents methylene.

6. A compound as defined in claim 1 wherein $R_c$ represents hydrogen.

7. A compound as defined in claim 1 wherein $R_c$ represents carboxy.

8. A compound as defined in claim 1 wherein $R_1$ represents hydrogen.

9. A compound as defined in claim 1 wherein $R_1$ represents methyl.

10. A compound as defined in claim 1 wherein p represents 1.

11. A compound as defined in claim 1 wherein p represents 2.

12. A compound as defined in claim 1 which is 1-fluoro-2,5-diamino-4-methylene-pentane or a pharmaceutically acceptable salt thereof.

13. A compound as defined in claim 1 which is 1-fluoro-2,5-diamino-4-oxo-pentane or a pharmaceutically acceptable salt thereof.

14. A compound as defined in claim 1 which is 2-fluoromethyl-2,5-diamino-4-oxo-pentanoic acid or a pharmaceutically acceptable salt thereof.

15. A compound as defined in claim 1 which is 2-fluoromethyl-2,5-diamino-4-methylene-pentanoic acid or a pharmaceutically acceptable salt thereof.

16. A compound as defined in claim 1 which is 1,1-difluoro-2,5-diamino-4-methylene-pentane or a pharmaceutically acceptable salt thereof.

17. An ornithine decarboxylase inhibiting pharmaceutical composition comprising from 10 mg to 300 mg of a compound as defined in claim 1 as an active ingredient with a pharmaceutically acceptable carrier or diluent.

18. A method of inhibiting ornithine decarboxylase in a patient in need thereof which comprises administering to said patient an effective ornithine decarboxylase inhibiting amount of a compound as defined in claim 1.

* * * * *

UNITED STATES PATENT AND TRADEMARK OFFICE
CERTIFICATE OF CORRECTION

PATENT NO. : 4,446,151

DATED : May 1, 1984

INVENTOR(S) : Fritz Gerhart and Viviane Van Dorsselaer

It is certified that error appears in the above-identified patent and that said Letters Patent are hereby corrected as shown below:

On the face of the patent, the priority information is missing and should read (under Foreign Application Priority Data) --August 19, 1981 (GB) United Kingdom 8125354 --.

At column 10, line 30, the patent reads "Formula VIII" and should read --Formula VII--.

At column 11, Formula X, the patent reads "R'$_7$O" and should read --R$_7$'O--.

At column 20, line 53, the patent reads "EcOEt" and should read --AcOEt--.

Signed and Sealed this

Fifteenth Day of March, 1988

Attest:

DONALD J. QUIGG

Attesting Officer

Commissioner of Patents and Trademarks